United States Patent [19]
Ishikawa

[11] Patent Number: 5,475,885
[45] Date of Patent: Dec. 19, 1995

[54] COUCH SYSTEM FOR X-RAY DIAGNOSIS

[75] Inventor: Naobumi Ishikawa, Otawara, Japan

[73] Assignee: Kabushiki Kaisha Toshiba, Kawasaki, Japan

[21] Appl. No.: 139,842

[22] Filed: Oct. 22, 1993

[30] Foreign Application Priority Data

Oct. 22, 1992 [JP] Japan .................................... 4-284540

[51] Int. Cl.⁶ .............................. A61B 6/04; A61G 7/00; A61G 13/00
[52] U.S. Cl. ...................... 5/601; 5/610; 108/5; 108/8; 108/10; 378/209
[58] Field of Search ........................ 5/601, 610; 378/209; 108/5, 7, 8, 10

[56] References Cited

U.S. PATENT DOCUMENTS

| | | | |
|---|---|---|---|
| 2,692,173 | 10/1954 | Lowitzsch | 5/601 |
| 3,240,935 | 3/1966 | Dougall | 378/209 |
| 3,302,022 | 1/1967 | Brenner et al. | 108/5 |
| 4,603,845 | 8/1986 | Schmedemann | 5/601 |
| 4,615,042 | 9/1986 | Schmedemann | 5/601 |
| 4,841,585 | 6/1989 | Masuzawa | 5/610 |
| 4,908,844 | 3/1990 | Masegawa | 5/601 |
| 5,131,105 | 7/1992 | Marwood et al. | 5/610 |

FOREIGN PATENT DOCUMENTS 1463105  11/1966  France ..................................... 378/209

*Primary Examiner*—Alexander Grosz
*Attorney, Agent, or Firm*—Oblon, Spivak, McClelland, Maier, & Neustadt

[57] ABSTRACT

A patient couch for an X-ray diagnosis comprises a base portion to be fixed to a floor of an X-ray diagnosis room and a movable portion mounted to the base portion to be movable with respect to the base portion and having a table top on which a patient lies. A tilting mechanism is secured to the base portion for vertically tilting the movable portion with respect to the base portion. The base portion and the tilting mechanism each has a width, in a width direction of the table top, smaller than a width of the table top and disposed below the movable portion along a longitudinal direction of the table top at a portion apart from a central axis thereof in the longitudinal direction so as to provide a space between a substantial portion of the movable portion and the floor. The tilting mechanism is tilted about a central axis, which is positioned below a horizontal level of the table top, by an angle more than 85° at which the table top on which a patient lies takes a vertically standing attitude without being obstructed by the location of the base portion.

7 Claims, 11 Drawing Sheets

COUCH SYSTEM FOR X-RAY DIAGNOSIS

BACKGROUND OF THE INVENTION

The present invention relates to a couch system for an X-ray diagnosis and, more particularly, to a patient couch for an X-ray diagnosis having a tiltable table top.

An X-ray diagnosis system generally comprises a couch on which a patient lies to be subjected to the X-ray diagnosis, an X-ray irradiation unit and an image receiving unit through which the X-ray transmitting the patient is imaged to thereby obtain an X-ray perspective image of a desired portion of the patient, preferably, on a display unit.

FIG. 11 represents examples of conventional various couches for the X-ray diagnosis, in which FIG. 11A shows a couch called a bookie-table and FIG. 11B shows a couch called a stretcher having a liftable table top 101. However, when the X-ray diagnosis is carried out, since it is necessary to move a portion of a patient to be subjected to the X-ray diagnosis to a predetermined position by constructing the couch to be vertically and horizontally movable with respect to the X-ray irradiation unit or image receiving unit. Thus, these couches of FIGS. 11A and 11B are not suitable for such X-ray diagnosis.

FIG. 11C shows a couch so-called an operation table and FIG. 11D shows a couch called a catheter table, both in which table tops 102 and 103 are liftable vertically and movable horizontally. However, when a fluoroscopic image of a celom such as stomach or intestine is required, it is necessary to tilt a patient to a predetermined angle position with respect to the horizontal level to distribute a contrast medium in the celom in a desired range in an organ. However, this requirement cannot be sufficiently satisfied by the couches of the types or structures shown in FIGS. 11A to 11D.

Furthermore, FIG. 11E shows a couch for an X-ray diagnosis having a structure in which the table top 105 is tiltable and horizontally movable to allow a patient to be tilted. The couch of this type incorporates an image receiving unit 104, which is also tiltable in accordance with the tilting motion of the table top 105. However, as can be seen from the structure of FIG. 11E, in the conventional imaging receiving unit incorporating couch, it is difficult to move, below the table top 105, another image receiving apparatus other than the incorporated image receiving unit 104 in a longitudinal direction of the table top 105 because of the location of the image receiving unit 104 below the table top, thus being inconvenient. Furthermore, a table top tilting mechanism 106 occupying a relatively large space is disposed on a side of the table top 105, which obstructs the access of a patient or an operator to the table top 105 and the arrangement of other measuring or additional equipments near the table top 105, thus being also inconvenient. Still furthermore, since it is impossible to vertically elevate the table top 105, it is inconvenient for a patient to get on and off the table top 105.

SUMMARY OF THE INVENTION

An object of the present invention is to substantially eliminate the defects or drawbacks encountered in the prior art and to provide a couch system for an X-ray diagnosis capable of tilting a table top of the couch system and moving an X-ray source or an image receiving unit along the longitudinal direction of the table top.

Another object of the present invention is to provide a couch system for an X-ray diagnosis having a table top tilting mechanism having less volume so as not to obstruct the access or movement of a patient or an operator near the table top of the couch.

These and other objects can be achieved according to the present invention by providing a couch system for an X-ray diagnosis comprising:

a base portion to be fixed to a floor in an X-ray diagnosis room;

a movable portion mounted to the base portion to be movable with respect to the base portion and having a table top on which a patient lies; and a tilting mechanism secured to the base portion for vertically tilting the movable portion with respect to the base portion, wherein the base portion and the tilting mechanism each has a width, in a width direction of the table top, smaller than a width of the table top and disposed below the movable portion along a longitudinal direction of the table top at a portion apart from a central axis thereof in the longitudinal direction so as to provide a space between a substantial portion of the movable portion and the floor in the X-ray diagnosis room.

In a preferred embodiment, the tilting mechanism is tilted about a central axis, which is positioned below a horizontal level of the table top, by an angle more than 85° at which the table top on which a patient lies takes a vertically standing attitude without being obstructed by the location of the base portion.

The tilting mechanism may be incorporated in the base portion and comprises an electric motor, a speed reduction mechanism connected through a belt means to a driving shaft of the electric motor, a pinion secured to the speed reduction mechanism and a gear wheel secured to the movable portion of the couch system to be engaged with the pinion so that a driving force of the electric motor is transmitted to the movable portion to tilt the same.

The couch system may further comprise a first moving mechanism for horizontally moving the table top in a longitudinal direction thereof, a second moving mechanism for horizontally moving the table top in a width, i.e., lateral direction thereof and an elevating mechanism for vertically moving the table top in a perpendicular direction thereof. These mechanisms may be incorporated in the movable portion.

According to the couch system for the X-ray diagnosis of the characters described above, since the couch system is formed by the base portion mounted on the floor in the room and the movable portion mounted to be movable to the base portion at a portion shifted from the central axis in the longitudinal of the movable portion, i.e. table top on which the patient lies. Accordingly, a space is provided below the substantial portion of the table top between it and the floor so that other equipment or unit such as X-ray imaging apparatus can be freely moved below the table top along the longitudinal direction thereof.

Furthermore, since the tilting mechanism for tilting the movable portion is also provided on the longitudinal side of the movable portion, this location does not also prevent the provision of the space below the movable portion and allow the tilting mechanism to rotate vertically more than 85°.

The horizontally moving mechanisms and the elevating mechanism can be additionally provided for horizontally and vertically moving the table top.

The further nature and features of the present invention will be made more clear from the following descriptions made with reference to the accompanying drawings.

BRIEF DESCRIPTION OF THE DRAWINGS

In the accompanying drawings:

FIG. 1 shows a couch system, on which a patient lies, for an X-ray diagnosis according to the present invention, in which

DESCRIPTION OF THE PREFERRED EMBODIMENT

An embodiment of a couch system for an X-ray diagnosis according to the present invention will be described hereunder with reference to the accompanying drawings.

Figure 1A:
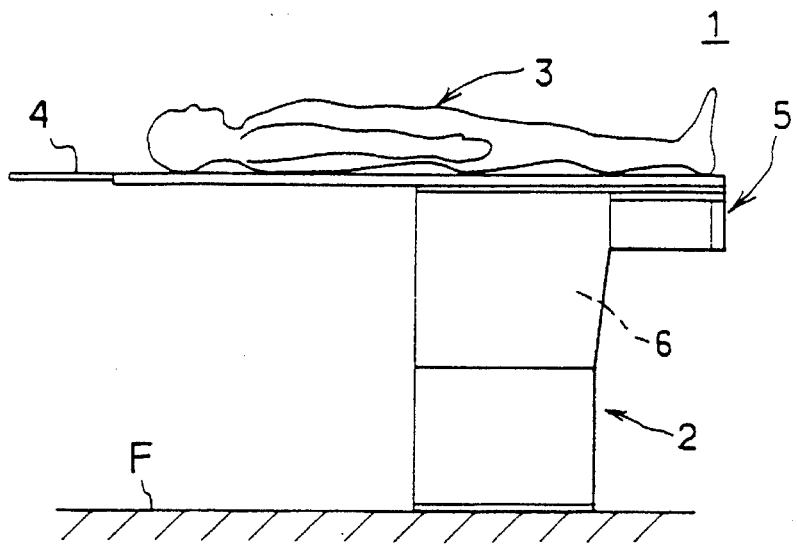
FIG. 1A is a side view of the couch system.
Figure 1B:
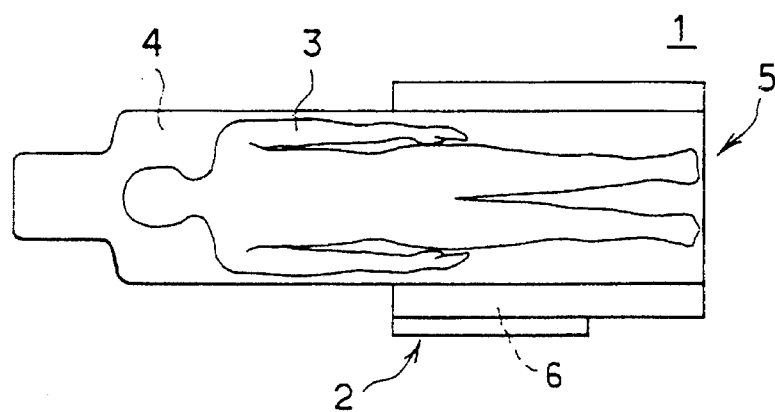
FIG. 1B is a plan view thereof and FIG. 1C is a front view thereof.
Figure 1C:
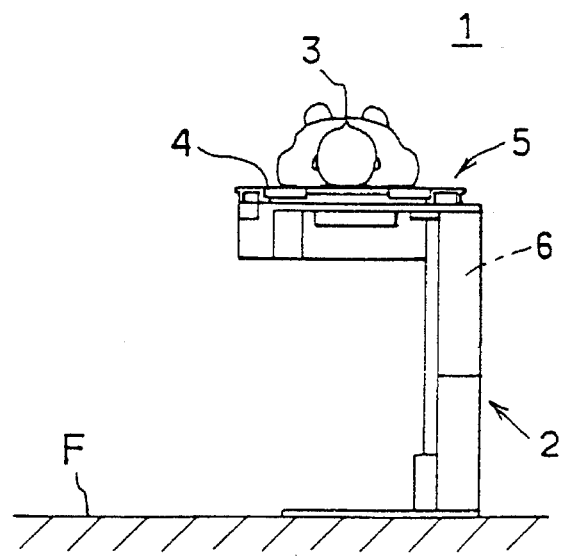

First, referring to FIGS. 1A to 1C, a couch system, called merely couch 1 hereinlater, for an X-ray diagnosis of the present invention is provided with a base, i.e. fixed, portion 2 to be settled on a predetermined position of a floor of an X-ray diagnosis room and a movable portion 5 mounted to the base portion 2 and having a table top 4 on which an object, such as a patient, 3 to be diagnosed, lies. The couch 1 is further provided with a tilting mechanism 6 for tilting the movable portion 5 with respect to the base portion 2. The tilting mechanism 6 and the base portion 2 are disposed between the floor and the movable portion 5 on one longitudinal side thereof by shifting their locations from the longitudinal central axis of the table top, as shown in FIG. 1C, so that another mechanism or unit such as image receiving unit can be freely moved below the movable portion 5 having the table top 4 along its longitudinal direction.

Figure 2:
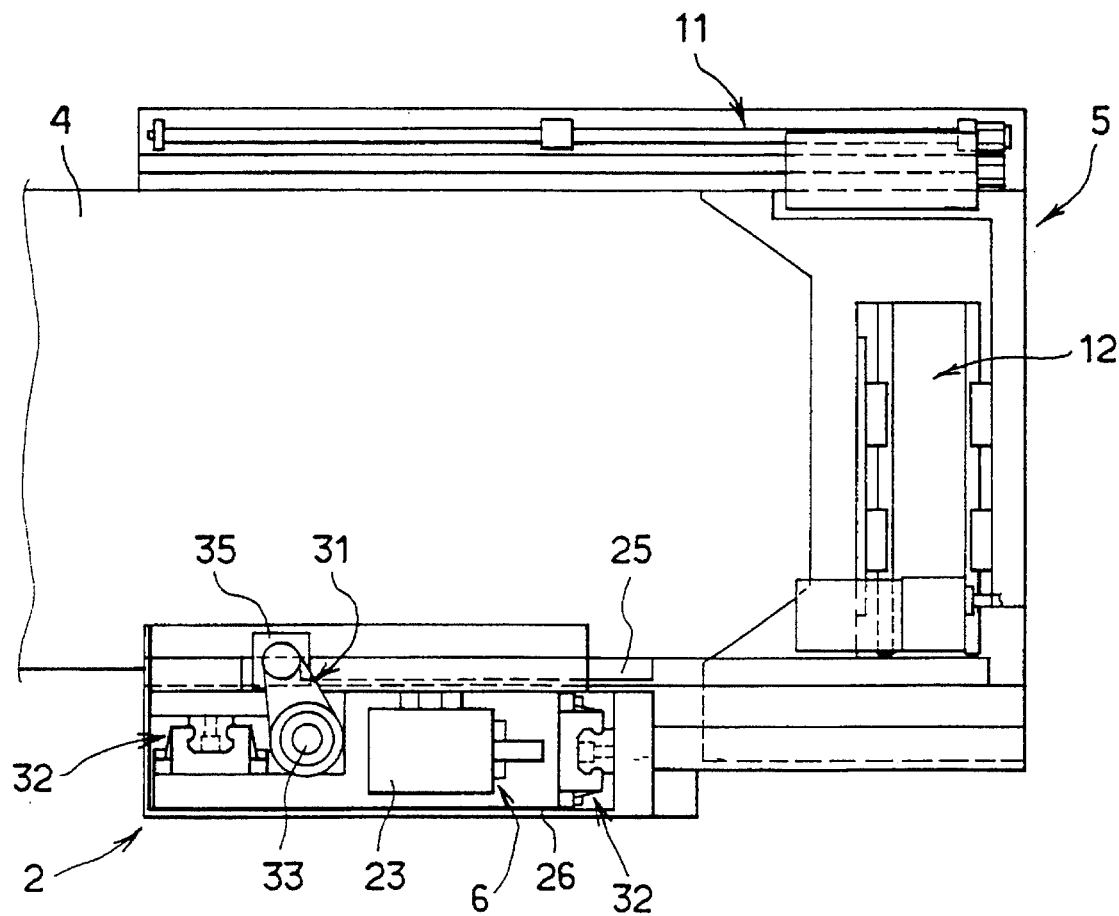
FIG. 2 is a plan view of the couch system of FIG. 1 for showing an inner structure thereof.

The movable portion 5 is, as shown in FIG. 2, provided with a first moving mechanism 11 for horizontally moving the table top 4 along the longitudinal direction thereof and a second moving mechanism 12 for horizontally moving the table top 4 along the width direction thereof.

Figure 3:
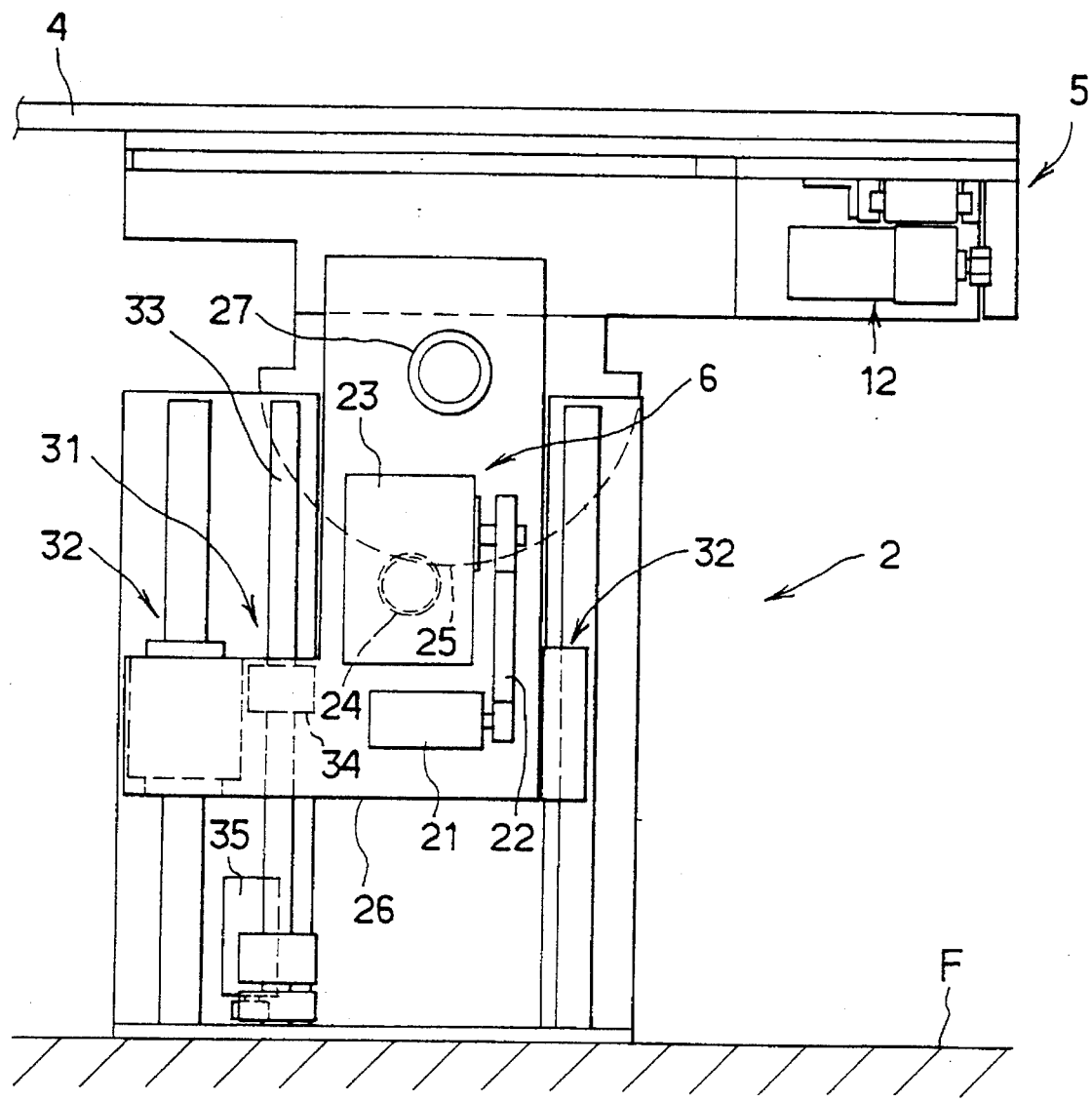
FIG. 3 is a side view of the couch system of FIG. 1 for showing an inner structure thereof.
Figure 4:
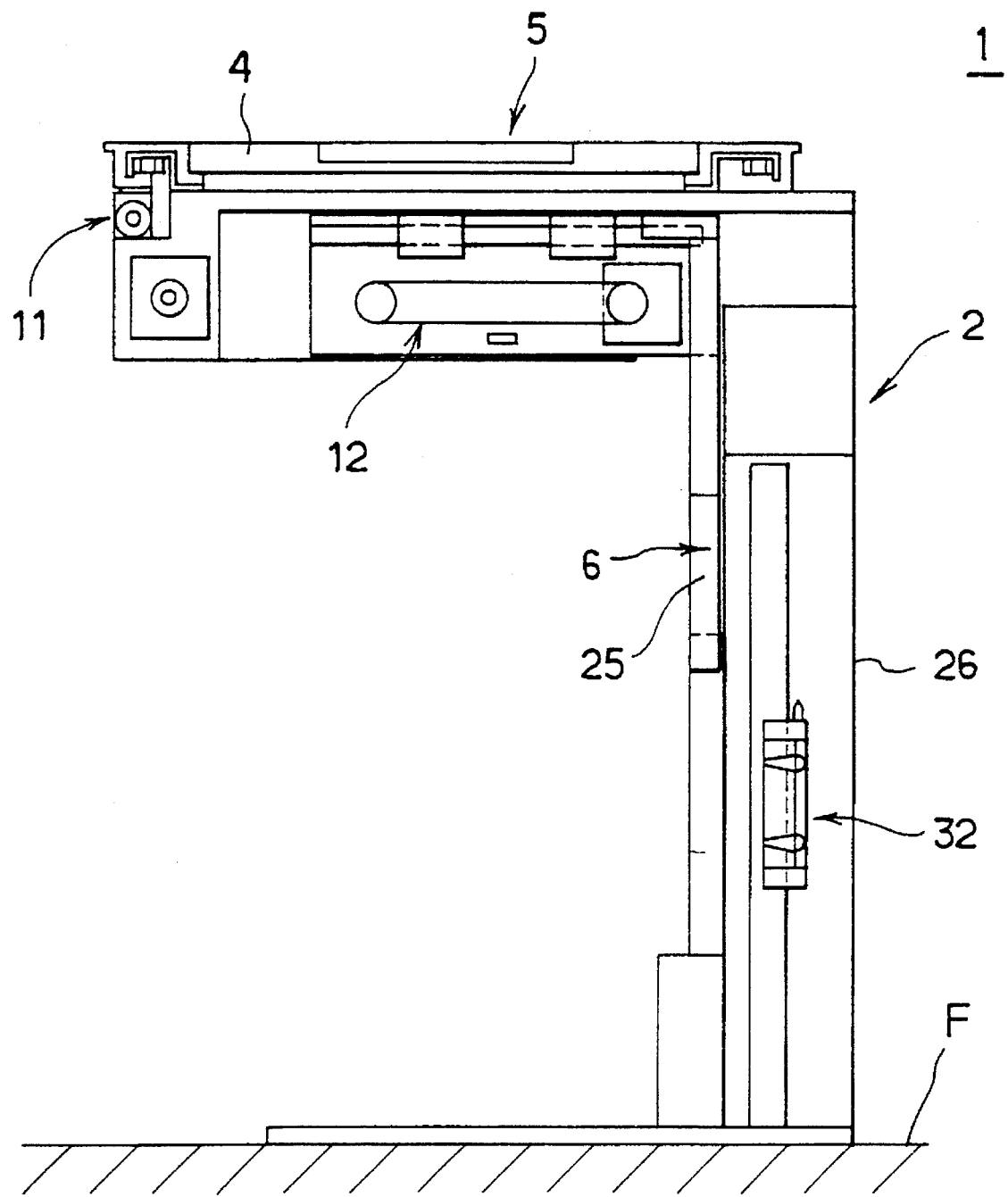
FIG. 4 is a front view of the couch system of FIG. 1 for showing an inner structure thereof.

Next, referring to FIGS. 2 to 4, the tilting mechanism 6 comprises an electric motor 21, a belt 22, a speed reduction mechanism 23 and a pinion 24. The driving force of the motor 21 is transmitted to a gear wheel 25 secured to the movable portion 5 through the belt 22, the speed reduction mechanism 23 and the pinion 24 in this order to thereby tilt or rotate the movable portion 5 about a predetermined horizontal axis. The motor 21 and the speed reduction mechanism 23 are fixedly mounted to a frame 26 to which the movable portion 5 is mounted to be rotatable through a bearing means 27 provided for the frame 26.

The base portion 2 is provided with a guide mechanism 32 for guiding an elevating motion of the frame and an elevating mechanism 31 secured to the frame for vertically elevating the movable portion 5. The elevating mechanism 31 includes an electric motor 35 having a rotation shaft 33 so as to extend perpendicularly. A screw groove is formed to the rotation shaft 33 and a nut means 34 secured to the frame 26 is engaged with this screw groove, whereby the driving force is transmitted through this structure to the frame 26 as a force for elevating the elevating mechanism 31 together with the frame 26. As can be seen from FIG. 4, the base portion 2 of the couch 1 in which the elevating mechanism 31 is incorporated is fixed to the floor F of an X-ray diagnosis room and the movable portion 5 is movably mounted to the base portion 2 to a portion apart from the central axis in the longitudinal direction of the table top 4, thus providing a space between the table top 4 and the floor in the X-ray diagnosis room.

Figure 5A:
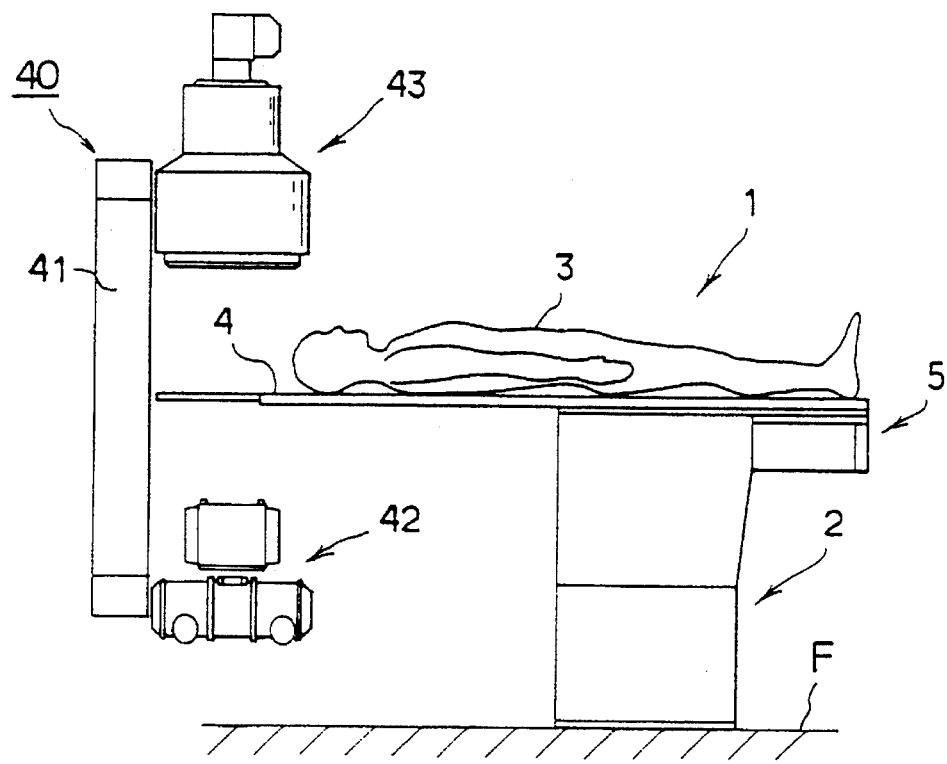
FIGS. 5A and 5B are side and front views showing a condition in an X-ray imaging operation to the couch system of FIG. 1.
Figure 5B:
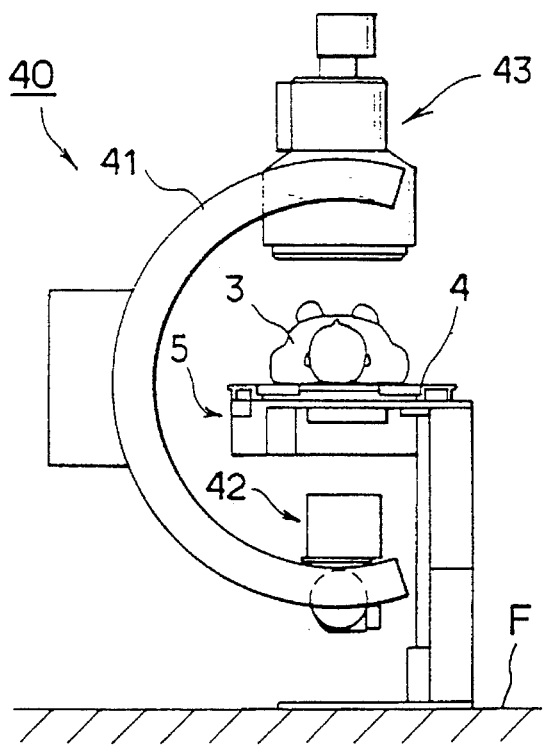

Further, as shown in FIG. 5, an X-ray imaging or irradiating unit 40 is disposed near the couch 1. The X-ray imaging unit 40 comprises a C-arm mechanism 41, an X-ray tube 42 secured to one end of the C-arm mechanism 41 and an image receiving unit 43 secured to the other end of the C-arm mechanism 41. In the illustrated embodiment, the X-ray tube 42 is secured to the lower side end of the C-arm mechanism 40. The imaging unit 40 may be movably settled on the floor or ceiling, in a certain case, or movably mounted to the couch itself.

When an X-ray imaging operation is carried out to a patient 3 on the table top 4 of the couch 1 for the X-ray diagnosis by utilizing the X-ray imaging unit 40, the X-ray tube 42 and the imaging receiving unit 43 are moved so that a patient lying on the table top 4 of the couch 1 is interposed therebetween. In this operation, as described above, since, the base portion 2 and the movable portion 5 of the couch 1 are positioned so as to provide a space below the substantial portion of the table top 4, the X-ray-tube 42 can be freely moved horizontally along the longitudinal direction of the table top 4.

Figure 6:
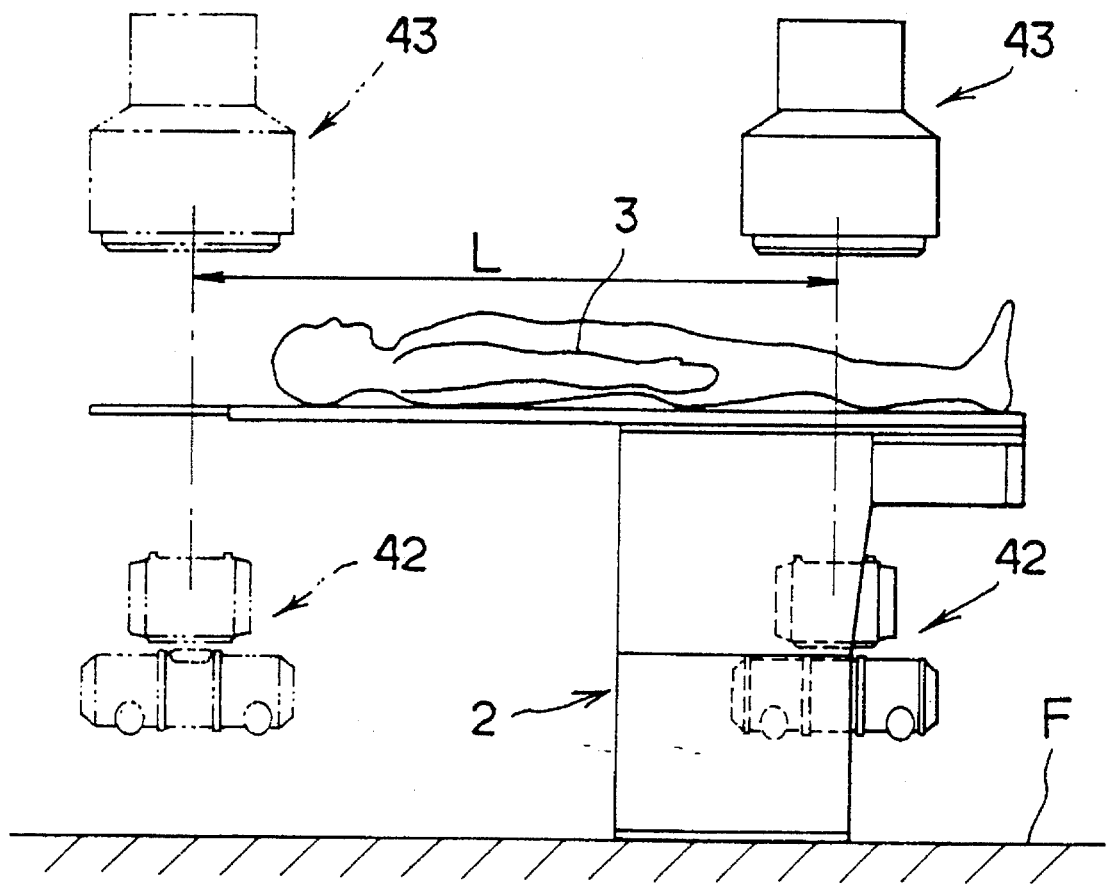
FIG. 6 is a side view showing a condition in which an X-ray tube and an image receiving unit are horizontally moved.
Figure 7A:
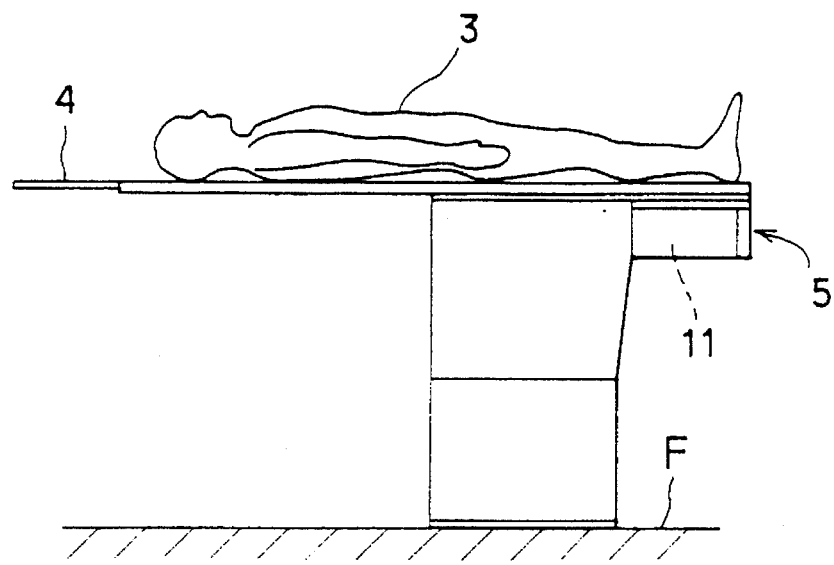
FIGS. 7A and 7B are side views showing moving states of the table top in the longitudinal direction thereof.
Figure 7B:
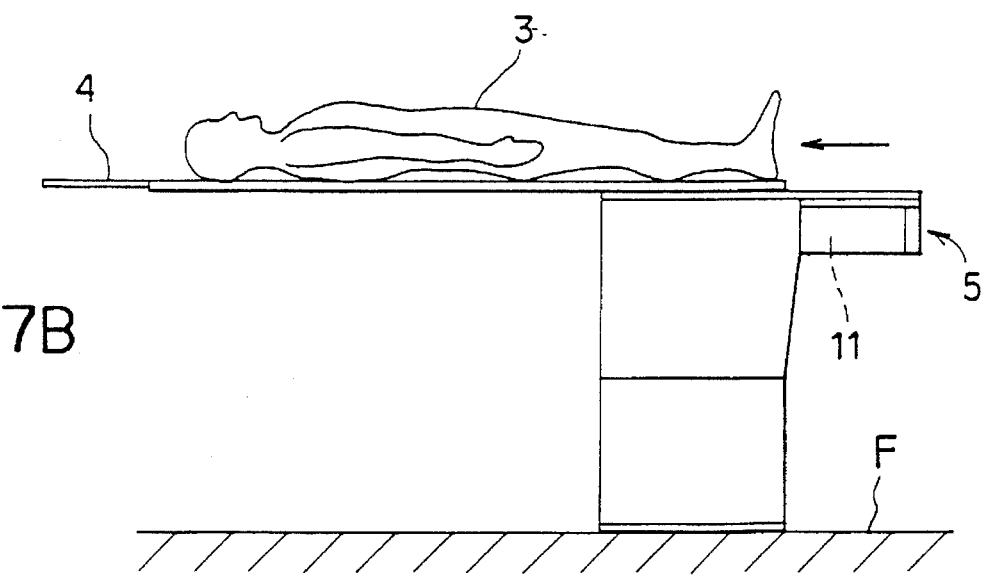
Figure 8A:
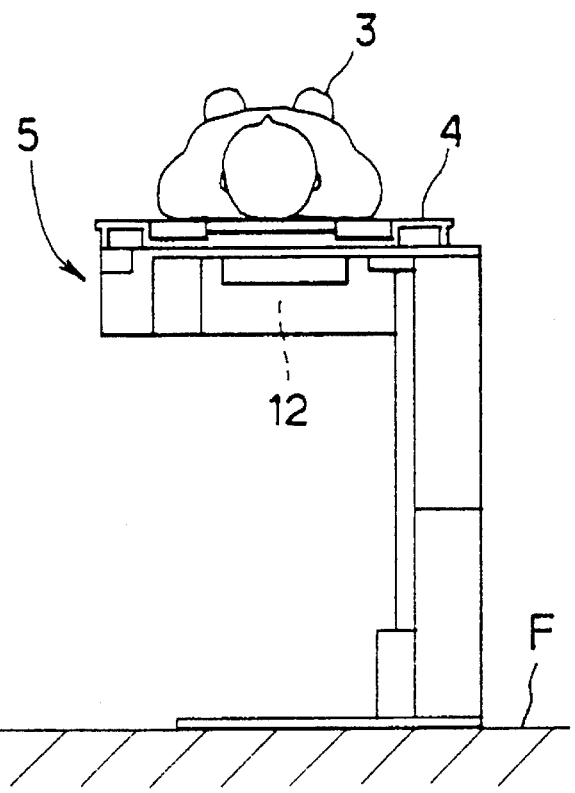
FIGS. 8A and 8B are side views showing moving states of the table top in the width direction thereof.
Figure 8B:
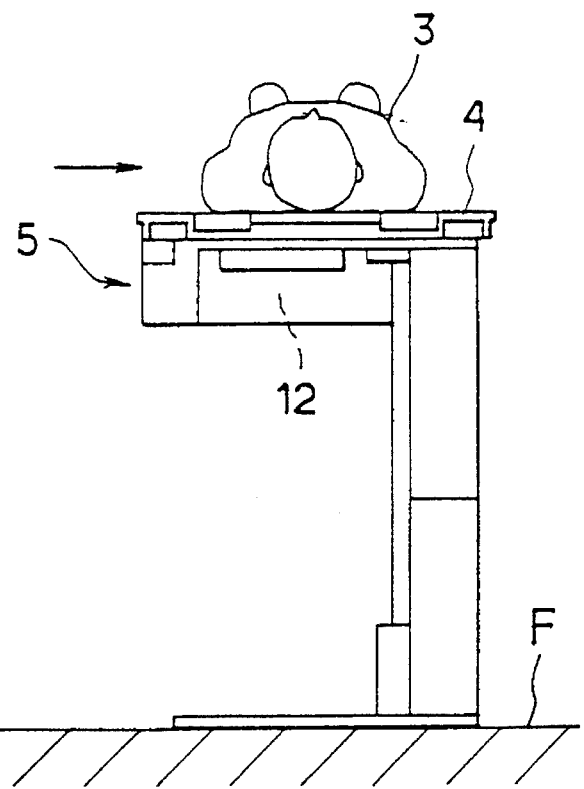

FIG. 6 shows a state in which the X-ray tube 42 and the image receiving unit 43 are moved horizontally by a distance L along the longitudinal direction of the patient 3 laying on the table top. FIGS. 7 and 8 show states respectively in which the driving mechanisms 11 and 12 disposed in the movable portion 5 of the couch 1 to thereby move the table top 4 along the longitudinal and width directions of the couch 1.

Figure 9:
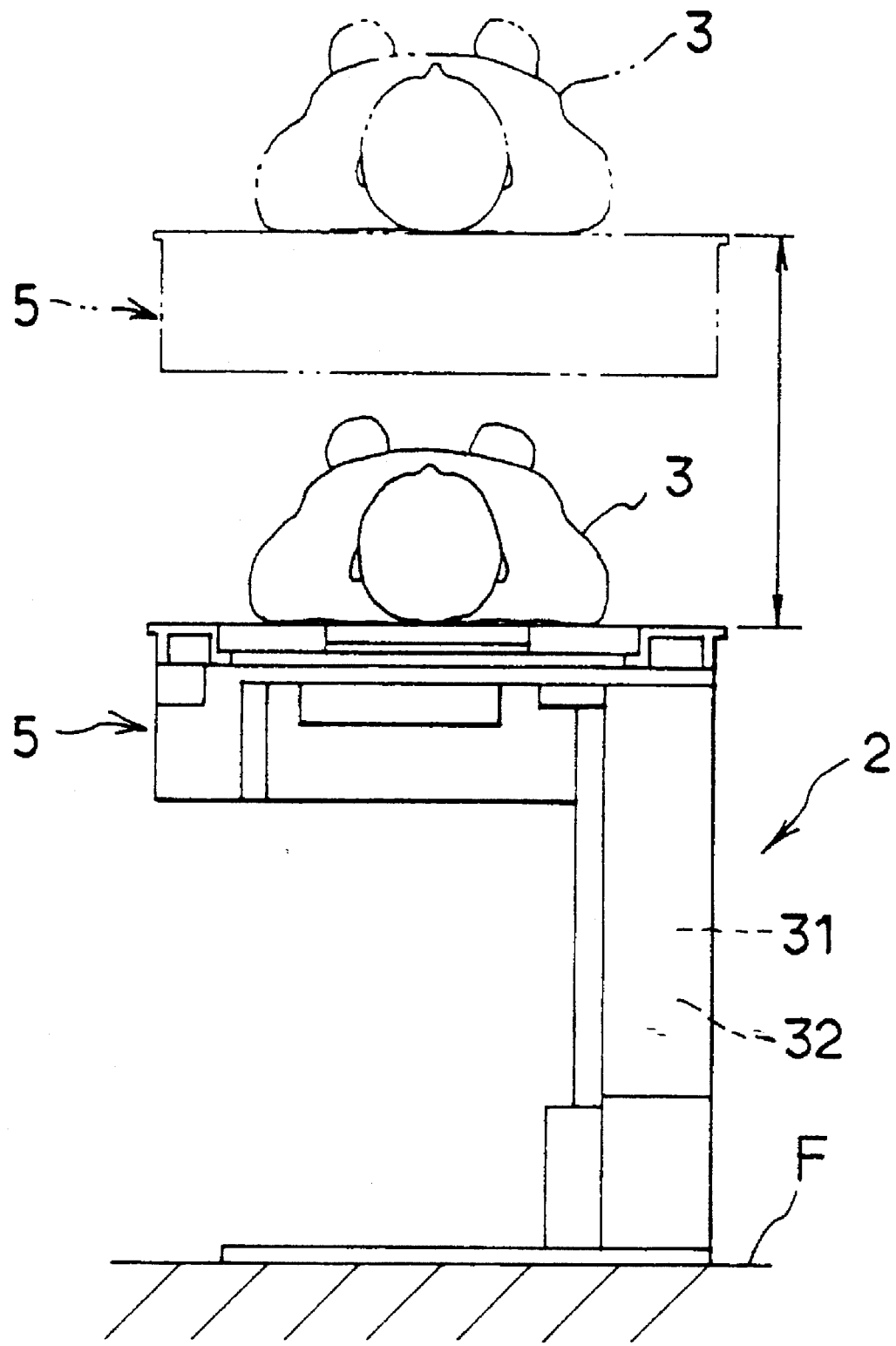
FIG. 9 is a front view showing a condition that the table top of the couch system of FIG. 1 is elevated upward.

On the other hand, FIG. 9 shows a state in which the elevating mechanism 31 incorporated in the fixed base portion 2 is elevated along the guide mechanism 32 to thereby vertically move the movable portion 5.

Figure 10:
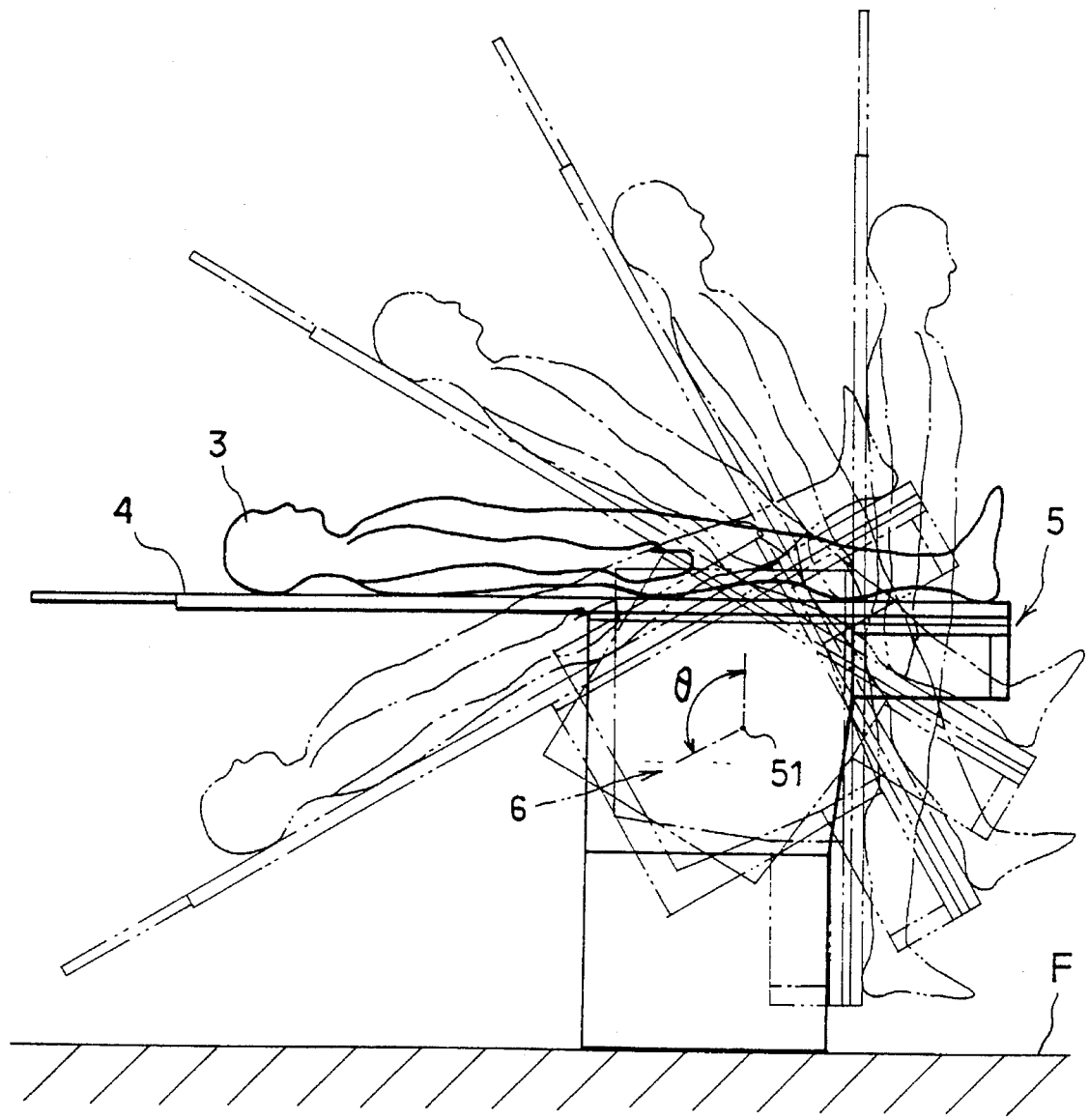
FIG. 10 is a view showing a vertically rotating or tilting condition of the table top of the couch system of FIG. 1.
Figure 11A:
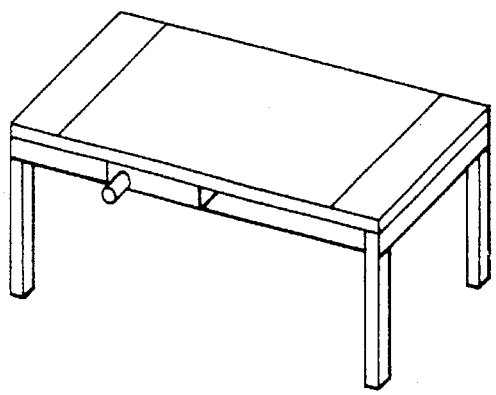
FIGS. 11A to 11E are perspective views showing conventional couches for the X-ray diagnosis.
Figure 11B:
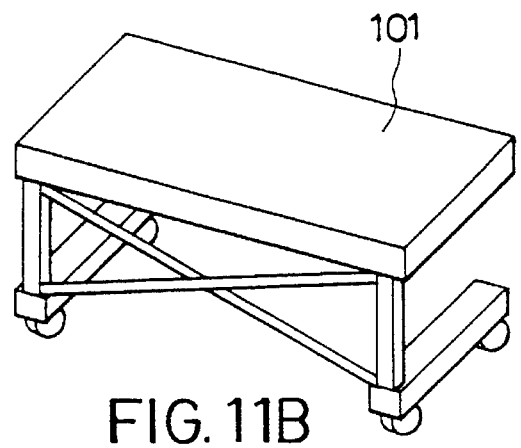
Figure 11C:
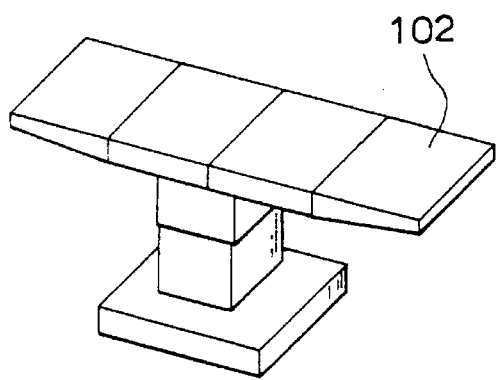
Figure 11D:
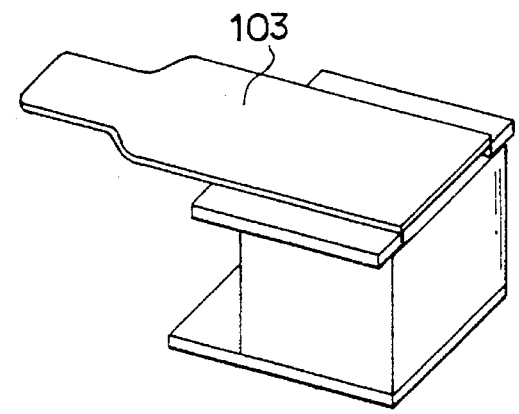
Figure 11E:
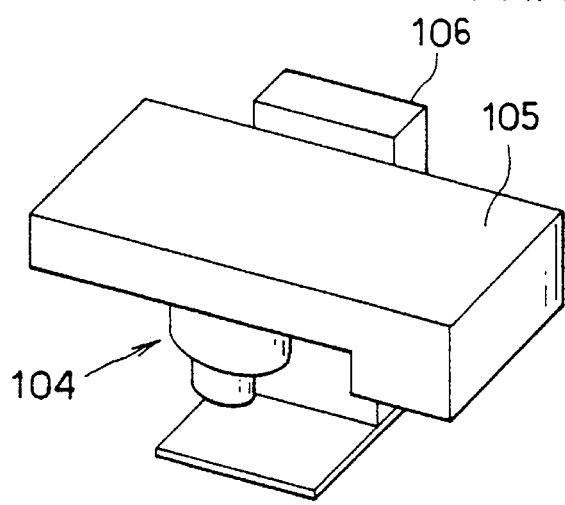

FIG. 10 shows a state in which the movable portion 5, i.e. table top 4 on which a patient 3 lies is tilted or rotated in a tiltable angle range θ about a rotation center 51 by the operation of the tilting mechanism 6. As can be seen from FIG. 10, the position of the rotation center 51, that is, the position of the bearing 27, is adjusted so that the side portion of the patient 3 on the table top 4 is not concealed by the base portion 2 at the standing attitude of the patient 3.

As described hereinabove, according to the X-ray diagnosis of the present invention, since the base portion 2 in which the tilting mechanism 6 is also incorporated is positioned on and along the longitudinal side, apart from the central axis, of the movable portion 5, the movable portion 5 can be freely tilted or rotated in the allowable angle range θ over 90° including the standing position thereof. Thus, the medical workings such as celom imaging and intervetional radiology (IVR) therapy under fluorscopy can be be remarkably improved.

Furthermore, since the space between the table top of the couch and the floor can be ensured regardless of the tilted position of the movable portion, the X-ray imaging unit including the X-ray tube and the image receiving unit can be freely moved in and along this space without being obstructed by the location of the base portion including the movable portion elevating mechanism and tilting mechanism.

Further, it is to be noted that, in the foregoing embodiment, the couch system of the present invention includes the horizontally moving mechanisms, the elevating mechanism and the tilting mechanism, but the horizontally moving mechanisms and the elevating mechanism may be eliminated as occasion demands and that the present invention is not limited to the described embodiment and many other changes or modifications may be made without departing from the scope of the appended claims of the present invention.

What is claimed is:

1. A couch system for an X-ray diagnosis provided with an X-ray diagnosis apparatus having a C-shaped arm member, comprising:

a base portion fixed to a floor in an X-ray diagnosis room;

a movable portion mounted to the base portion to be movable with respect to the base portion and having a table top on which a patient lies, said movable portion having a central longitudinal axis;

a tilting mechanism secured to the base portion and incorporated therein for vertically tilting substantially an entire structure of the movable portion with respect to the base portion, said tilting mechanism being driven by a first electric means;

a first moving mechanism for horizontally moving the table top in a longitudinal direction thereof;

a second moving mechanism for horizontally moving the table top in a lateral direction thereof; and an elevating mechanism driven by a second electric means for vertically moving the table top in a perpendicular direction thereof, wherein said base portion and said tilting mechanism have a thickness in a width direction of the table top smaller than a width of the table top and disposed below the movable portion along a longitudinal direction of the table top within the width of the movable portion and at a distance spaced from said central longitudinal axis thereof so as to provide a space between a substantial portion of the movable portion and the floor in the X-ray diagnosis room in which the C-shaped arm member is freely movable, said substantial portion comprising more than one-half the width and all of the length of the movable portion, and wherein said movable portion is tilted about a central axis which is positioned below a horizontal level of the table top.

2. A couch system according to claim 1, wherein said tilting mechanism is tilted about the central axis by an angle more than 85° at which the table top on which a patient lies takes a vertically standing attitude.

3. A couch system according to claim 2, wherein said movable portion is tilted without being obstructed by the location of the base portion.

4. A couch system according to claim 1, wherein said tilting mechanism comprises an electric motor, a speed reduction mechanism connected through a belt means to a driving shaft of the electric motor, a pinion secured to the speed reduction mechanism and a gear wheel secured to the movable portion to be engaged with the pinion so that a driving force of the electric motor is transmitted to the movable portion to tilt the same.

5. A couch system according to claim 1, wherein said first moving mechanism is incorporated in said movable portion.

6. A couch system according to claim 1, wherein said second moving mechanism is incorporated in said movable portion.

7. A couch system according to claim 1, wherein said elevating mechanism is incorporated in said base portion.

* * * * *